United States Patent
Hastings et al.

(10) Patent No.: US 8,019,435 B2
(45) Date of Patent: Sep. 13, 2011

(54) CONTROL OF ARTERIAL SMOOTH MUSCLE TONE

(75) Inventors: Roger Hastings, Maple Grove, MN (US); William J. Drasler, Minnetonka, MN (US); Vitaly Shapovalov, New Hope, MN (US); Mark Schroeder, West Fargo, ND (US); Anupama Sadasiva, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1024 days.

(21) Appl. No.: 11/381,238

(22) Filed: May 2, 2006

(65) Prior Publication Data
US 2007/0260281 A1     Nov. 8, 2007

(51) Int. Cl.
*A61N 1/04* (2006.01)
(52) U.S. Cl. .......................................... 607/115
(58) Field of Classification Search ................... 607/116, 607/122, 44, 115
See application file for complete search history.

(56) References Cited

U.S. PATENT DOCUMENTS

| | | | |
|---|---|---|---|
| 5,411,540 A | 5/1995 | Edell et al. | |
| 5,800,464 A | 9/1998 | Kieval | |
| 5,814,079 A | 9/1998 | Kieval | |
| 6,106,546 A | 8/2000 | Gregory | |
| 6,347,247 B1 * | 2/2002 | Dev et al. | 607/2 |
| 6,571,127 B1 * | 5/2003 | Ben-Haim et al. | 607/40 |
| 6,801,286 B2 | 10/2004 | Yamaguchi et al. | |
| 6,865,416 B2 | 3/2005 | Dev et al. | |
| 2002/0010461 A1 | 1/2002 | KenKnight et al. | |
| 2003/0055465 A1 | 3/2003 | Ben-Haim et al. | |
| 2003/0187340 A1 | 10/2003 | Kenknight et al. | |
| 2003/0216792 A1 | 11/2003 | Levin et al. | |
| 2004/0186546 A1 | 9/2004 | Mandrusov et al. | |
| 2005/0101697 A1 | 5/2005 | Morihiro et al. | |
| 2005/0171575 A1 | 8/2005 | Dev et al. | |
| 2006/0030887 A1 | 2/2006 | Letort et al. | |
| 2006/0142801 A1 | 6/2006 | Demarais et al. | |

FOREIGN PATENT DOCUMENTS

| | | |
|---|---|---|
| WO | WO 98/42403 | 10/1998 |
| WO | WO-2007/131015 A2 | 11/2007 |

OTHER PUBLICATIONS

"European Application Serial No. 7783078.4, Office Action mailed May 13, 2009", 3 pgs.
"European Application Serial No. 7783078.4, Office Action mailed Aug. 3, 2010", 4 pgs.
"European Application Serial No. 7783078,4, Response filed Sep. 15, 2009 to Office Action mailed May 13, 2009", 5 pgs.
"European Application Serial No. 7783078.4, Response filed Dec. 13, 2010 to Office Action mailed Aug. 3, 2010", 9 pgs.
"International Application Serial No. PCT/US2007/067989, International Search Report mailed Dec. 7, 2007", 4 pgs.

(Continued)

*Primary Examiner* — Eric D. Bertram
(74) *Attorney, Agent, or Firm* — Schwegman, Lundberg & Woessner, P.A.

(57) ABSTRACT

An apparatus for locally controlling smooth muscle tone includes a first electrode for insertion into an artery; a barrier for preventing the first electrode from contacting an arterial wall; a second electrode; a power supply; and a controller for coupling the power supply to the electrodes. The controller is configured to cause the electrode to maintain a waveform for controlling polarization of smooth muscle tone.

17 Claims, 14 Drawing Sheets

OTHER PUBLICATIONS

"International Application Serial No. PCT/US2007/067989, Written Opinion mailed Dec. 7, 2007", 6 pgs.

"Japanese Application Serial No. 2009-510044, Amendment filed Oct. 15, 2010", (w/ English Translation of Amended Claims), 7 pgs.

Dev, N. B, et al., "Intravascular Electroporation Markedly Attenuates Neointima Formation After Balloon Injury of the Carotid Artery in the Rat", *Journal of Interventional Cardiology*, 13(5), (Oct. 2000), 331-338.

* cited by examiner

CONTROL OF ARTERIAL SMOOTH MUSCLE TONE

FIELD OF DISCLOSURE

This disclosure relates to medical devices, and in particular, to devices for controlling smooth muscle tone.

BACKGROUND

The arteries and arterioles (collectively referred to as "arterial blood vessels") throughout the body are lined with smooth muscle. This smooth muscle regulates the flow of arterial blood. Relaxation of the smooth muscle dilates the arterial blood vessel, permitting free flow of blood. Contraction of the smooth muscle constricts the arterial blood vessel, thereby constricting the flow of blood.

Relaxation and contraction of smooth muscle also have an effect on blood pressure. Relaxation increases the volume of the arterial blood vessel, thereby reducing blood pressure. Such blood vessels are said to be "vasodilated." Contraction reduces the volume of the arterial blood vessel, thereby increasing blood pressure. Such blood vessels are said to be "vasoconstricted."

When a person suffers a heart attack, a tendency exists for blood pressure to fall. In an effort to counteract this tendency, the autonomic nervous system causes smooth muscles throughout much of the vascular system to contract. The resulting system-wide vasoconstriction raises blood pressure.

Among the vasoconstricted arterial blood vessels are the renal artery and its associated renal arterioles. Constriction of these arterial blood vessels hampers the kidneys' ability to remove excess fluid. As a result, blood volume increases beyond normal levels. The heart, which is already in weakened condition, encounters difficulty pumping this quantity of blood. As a result, this excess blood can accumulate in the heart and cause the heart to pump less efficiently. In addition, the excess fluid can be excreted into the lungs, resulting in pulmonary congestion, which in turn may cause difficulty breathing.

It is possible to provide drugs that reduce blood pressure. But these drugs act systemically and therefore counteract what is, for most parts of the arterial system, an effective response to the drop in blood pressure caused by heart failure.

It is also known that smooth muscle tone may be locally controlled by contacting the arterial wall with an electrode and providing a suitable electrical stimulation. However, this requires that the arterial blood vessel be large enough to permit insertion of an electrode. As a result, it is difficult to use this method to control smooth muscle tone in the arterioles. Moreover, there are often a great many arterioles that will need to be vasodilated. A procedure that relies on contacting the wall of each such arteriole would thus be impractical.

SUMMARY OF INVENTION

The invention is based on the recognition that because the blood is electrically conductive, one can effectively broadcast instructions to smooth muscle tissue lining the arterial blood vessels by using the blood vessels themselves as a communication channel. This is achieved by identifying the location of one or more targeted blood vessels and placing a pair of electrodes in such a way that the path of least resistance for current flowing between the two electrodes includes the targeted blood vessel(s).

In one aspect, the invention features an apparatus for locally controlling smooth muscle tone. The apparatus includes a first electrode for insertion into an artery; a barrier for preventing the first electrode from contacting an arterial wall; a second electrode; a power supply; and a controller for coupling the power supply to the electrodes. The controller is configured to cause the electrode to maintain a waveform for controlling polarization of smooth muscle tone.

Embodiments include those in which the first electrode includes a stent, and those in which the first electrode includes a distal tip of a catheter.

Other embodiments include those in which the second electrode includes conducting pads for placement on the skin of a patient, and those in which the second electrode includes a distal tip of a catheter.

Additional embodiments include those in which the barrier includes a stent defining a lumen for receiving the first electrode, those in which the barrier includes a housing surrounding the first electrode, those in which the barrier includes a cage surrounding the first electrode, and those in which the barrier includes a pair of bumpers disposed on either side of the electrode.

Among the various embodiments are those in which the controller is configured to generate a waveform having pulses of alternating polarity, those in which the controller is configured to generate a waveform having pulses of a single polarity, and those in which controller is configured to generate a waveform that is synchronized with the cardiac cycle.

Certain other embodiments include a sensor for providing data indicative of the cardiac cycle to the controller, and/or a local sensor for providing data indicative of blood pressure local to the first electrode.

In another aspect, the invention features a method for regulating smooth muscle tone within an arterial bed of a patient by inserting a first electrode into an artery of the patient; providing a second electrode at a location selected such that current from the first electrode to the second electrode traverses the arterial bed; and generating a voltage waveform between the first and second electrode. The voltage waveform is selected to control polarization of smooth muscle tissue within the arterial bed.

In some practices of the invention, providing a second electrode includes providing a surface electrode for placement on the patient's skin. In other practices, providing a second electrode includes inserting a second electrode into a patient's vein.

Some practices of the invention also include selecting the artery to be a renal artery, and/or selecting the location of the second electrode to be skin adjacent to the a kidney.

A variety of waveforms can be generated. In some practices, generating a voltage waveform includes generating a waveform having an excitation cycle and a cleaning cycle. In others, generating a waveform includes generating an excitation cycle that overlaps the diastole portion of the patient's cardiac cycle.

Additional practices of the invention include synchronizing the waveform with the patient's cardiac cycle.

Additional practices include selecting the arterial bed to be an arterial bed that serves a tumor, and/or selecting the arterial bed to include arteries feeding a hemorrhage and/or selecting the arterial bed to include the penile arteries.

Yet other practices of the invention include obtaining a measurement indicative of systemic hypertension, and generating the voltage waveform in response to the measurement.

Other practices of the invention include generating a positive voltage during the excitation cycle, and generating a negative voltage during the excitation cycle.

Other features and advantages of the invention will be apparent from the following detailed description, the claims, and the accompanying figures, in which:

BRIEF DESCRIPTION OF THE DRAWINGS

FIG. 12 shows a stimulation system that uses a stent as a barrier; and

DETAILED DESCRIPTION

Local control of smooth muscle tone in an arterial bed is achieved by causing electric current to flow through the arterial bed. The resulting current is sufficient in amplitude to locally control the polarization of smooth muscles throughout the arterial bed. Depending on the polarity of the current, smooth muscles can be locally depolarized or hyperpolarized.

Figure 1:
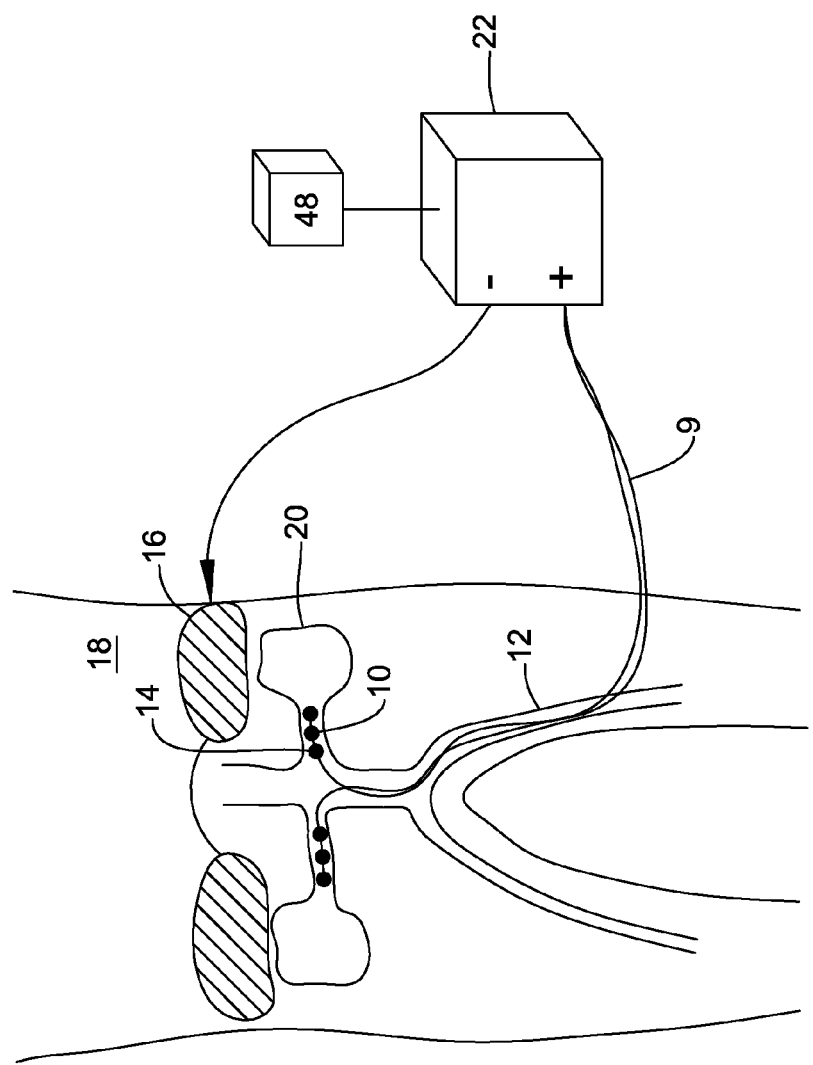
FIGS. 1, 12, and 13 show stimulation systems.

One embodiment, shown in FIG. 1, is intended to locally dilate arterial blood vessels that serve the renal system. This embodiment includes a catheter 9 having a first electrode 10 at its distal tip. The catheter 9 is inserted through a femoral artery 12 and maneuvered until the first electrode 10 reaches a proximal renal artery 14. A second electrode 16 is then placed on the skin 18 adjacent to the kidney 20.

The first and second electrodes 10, 16 are then connected to respective positive and negative terminals of a power supply 22. However, in other applications, in which one seeks to promote vasoconstriction rather than vasodilation, this polarity is reversed. The first and second electrodes 10, 16 are thus monopolar electrodes. However, bipolar or multipolar electrodes can also be used since there is no requirement that all terminals of an electrode be connected to a power supply 22.

In some embodiments, the first electrode 10 is a bare portion of an otherwise electrically insulated guide wire. However, in such cases, there remains a possibility of contact between the first electrode 10 and the arterial wall. Such contact would result in some current flowing into the arterial wall instead of remaining in the bloodstream to reach arterioles downstream from the first electrode 10.

FIG. 1 thus shows one representative embodiment of a catheter 9 having one or more electrodes 10 for placement within a blood vessel that feeds a targeted arterial bed. Current from the catheter-borne electrodes 10 flows through the arterial bed on its way to a return electrode pad placed on the patient's skin over the region supplied by the targeted arterial bed. To achieve vasodilation, the catheter-born electrode 10 is operated as an anode, and the return electrode pad 10 is operated as a cathode. To achieve vasoconstriction, the return electrode pad 10 is operated as an anode, and the catheter-borne electrode 10 is operated as a cathode. The catheter-borne electrode 10 and the return electrode pad 16 are configured so that the electric field lines, and therefore current flow, traverse the target arterial bed.

Figure 2:
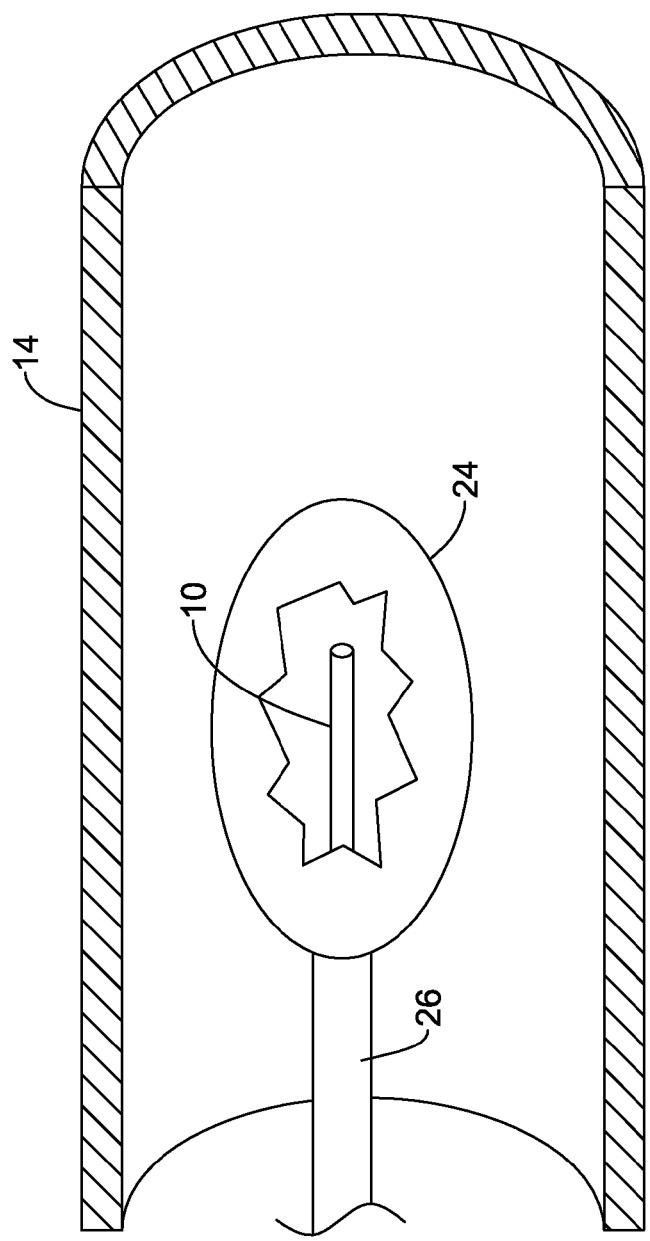
FIG. 2 shows a balloon enclosing the electrode from the stimulation systems of FIG. 1, 12, or 13.

In other embodiments a barrier surrounds the first electrode 10. A suitable barrier, shown in FIG. 2, is a balloon 24 such as those used in a balloon catheter. This balloon 24 prevents the first electrode 10 from actually contacting the arterial wall.

Figure 3:
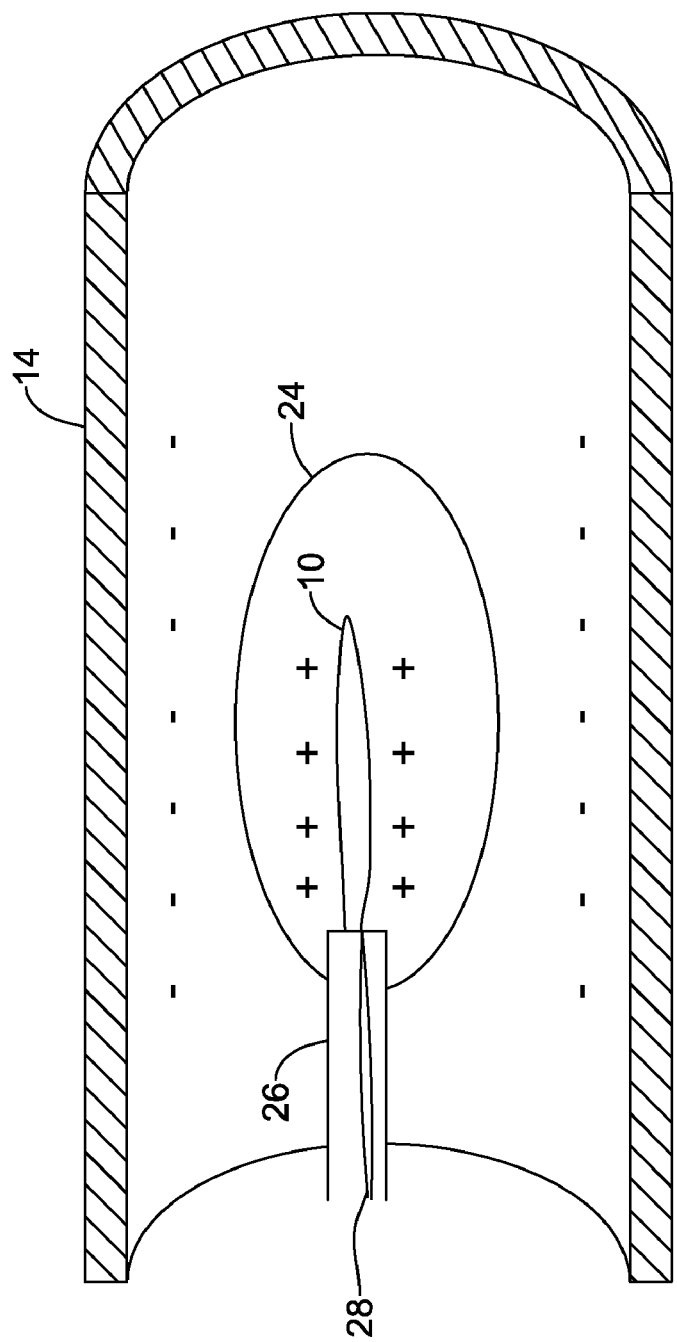
FIGS. 3 and 4 are longitudinal and transverse cross-sections of the balloon of FIG. 2.

FIG. 3 shows a longitudinal cross-section of a balloon catheter 26 with the balloon 24 fully deployed. In the configuration shown, the balloon 24 functions as a barrier to prevent direct contact between the electrode 10 and the wall of the artery 14. The electrode 10 supports an electric field, which in turn provides an electromotive force sufficient to propel current through the bloodstream between the first and second electrodes 10, 16.

Figure 4:
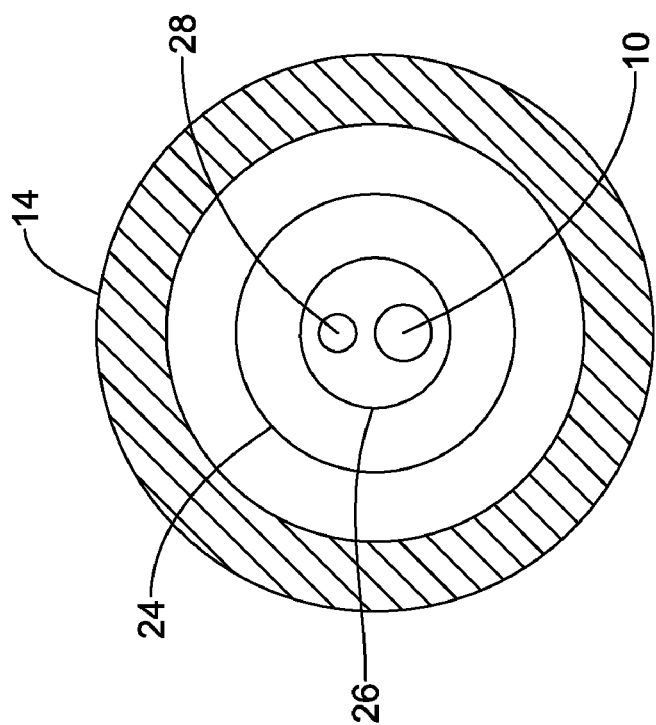

FIG. 4 shows a transverse cross-section of the balloon catheter 26 in FIG. 2. The balloon 24, in its deployed state, has a generally circular cross-section, the radius of which varies along the length thereof, with minima at proximal and distal ends of the balloon 24.

The balloon 24 is inflated with a fluid, which can be gas or liquid, and either electrically insulating or conductive. The pressure of this fluid is selected to provide sufficient turgidity to prevent the electrode 10 from contacting the balloon 24, but enough flexibility to avoid impairing a surgeon's ability to maneuver the catheter 26 through the vascular system.

The balloon 24 is typically made of a biocompatible material, such as latex or silicone. The interior of the balloon 20 is in fluid communication with a pump (not shown) that selectively inflates or deflates the balloon. For this purpose, a flexible tube 28 typically extends along the catheter 26 between the pump and the interior of the balloon 20.

While a balloon 24 as described above will tend to act as a barrier to low-frequency current, at higher frequencies, there may be capacitative coupling between the electrode 10 and the balloon 24. This, in turn, may cause sufficient charge to be on the surface of the balloon 24, in which case contact between the balloon 24 and the arterial wall may result in some current within the wall itself.

Figure 5:
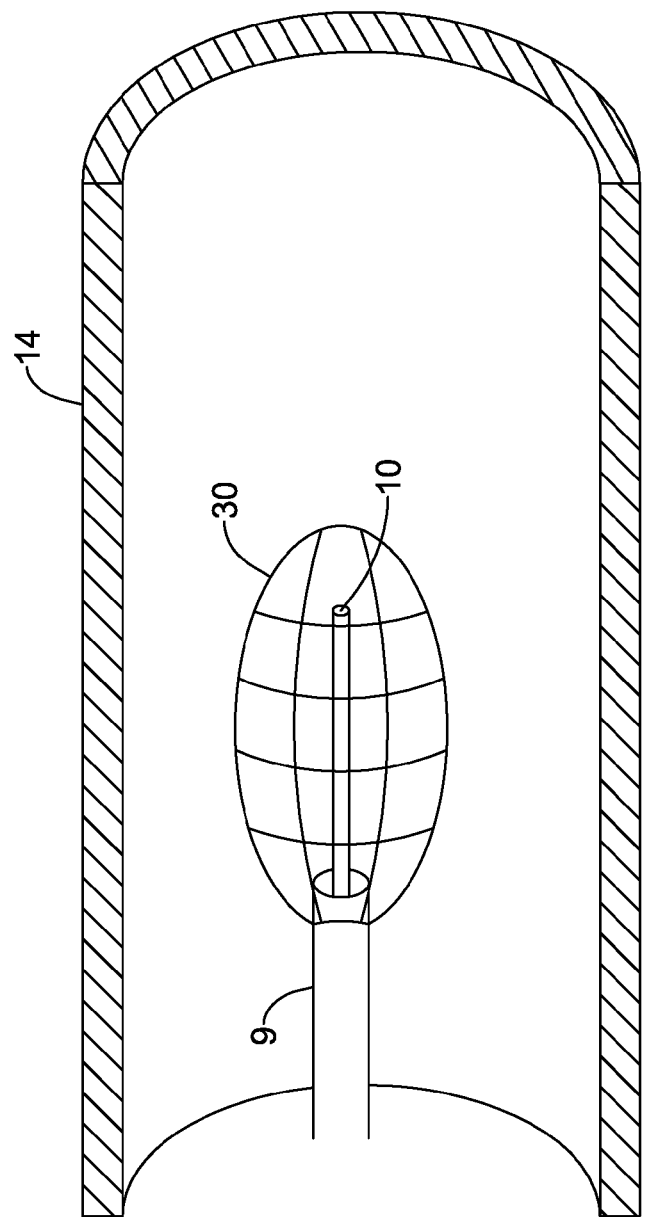
FIG. 5 shows an electrode surrounded by a cage.

Another example of a barrier is a mesh or net cage 30 such as that shown in FIG. 5. The cage 30 can be rigid, or slightly flexible, but with enough resistance to cushion the electrode 10 against accidentally contacting the cage 30. The cage 30 can be made of either an insulating, or a conductive material. However, if the cage 30 is made of a conductive material, it is best electrically isolated from the electrode 10, so that the potential at the electrode 10 need not match the potential of the cage 30.

The overall shape of the cage 30 is similar to that of the balloon 24 shown in FIGS. 2-4. This shape, which is generally ellipsoidal or ovaloid, provides a low profile while reducing the likelihood of trauma should the cage contact the arterial wall.

Figure 6:
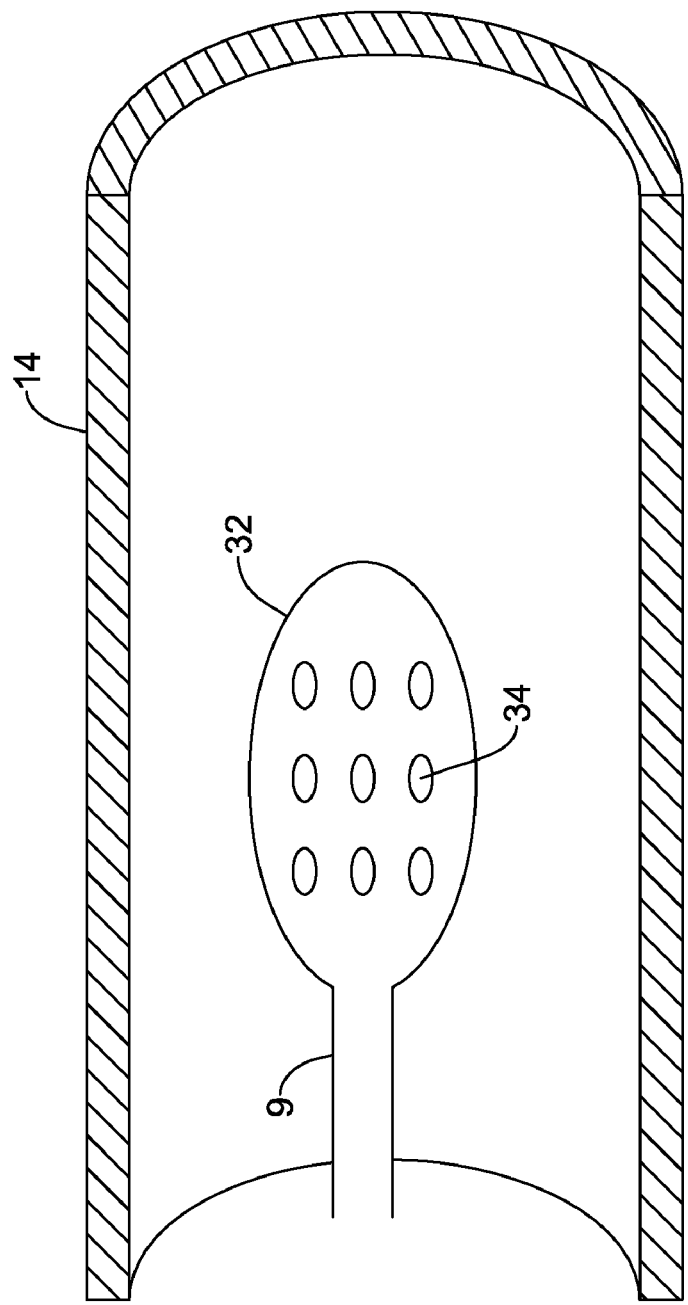
FIG. 6 shows an electrode surrounded by a housing.

Yet another example of a barrier, shown in FIG. 6, is a housing 32 that encloses the electrode 10. The housing can completely enclose the electrode 10, or it can have holes 34, as shown in FIG. 6, through which blood can enter and exit the housing 32, thereby providing direct electrical contact between the electrode and the blood. The housing 32 likewise has an ellipsoidal or ovaloid shape to provide both a low profile and to avoid trauma should the housing inadvertently contact the arterial wall.

Figure 7:
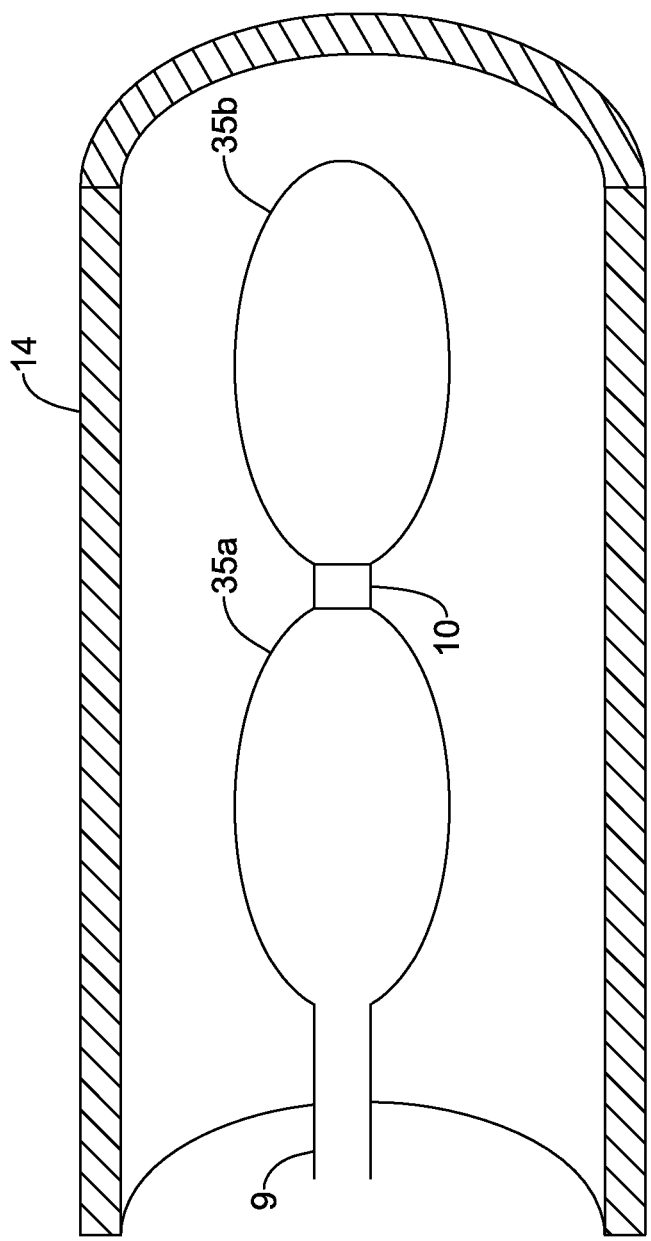
FIG. 7 shows an electrode protected by a pair of bumpers.

Another embodiment, shown in FIG. 7, includes a barrier in the form of a pair of bumpers 35a, 35b disposed proximal and distal to the first electrode 10. In this embodiment, the electrode 10 contacts the blood directly, while the bumpers 35a, 35b prevent the electrode 10 from contacting the arterial wall.

Figure 8:
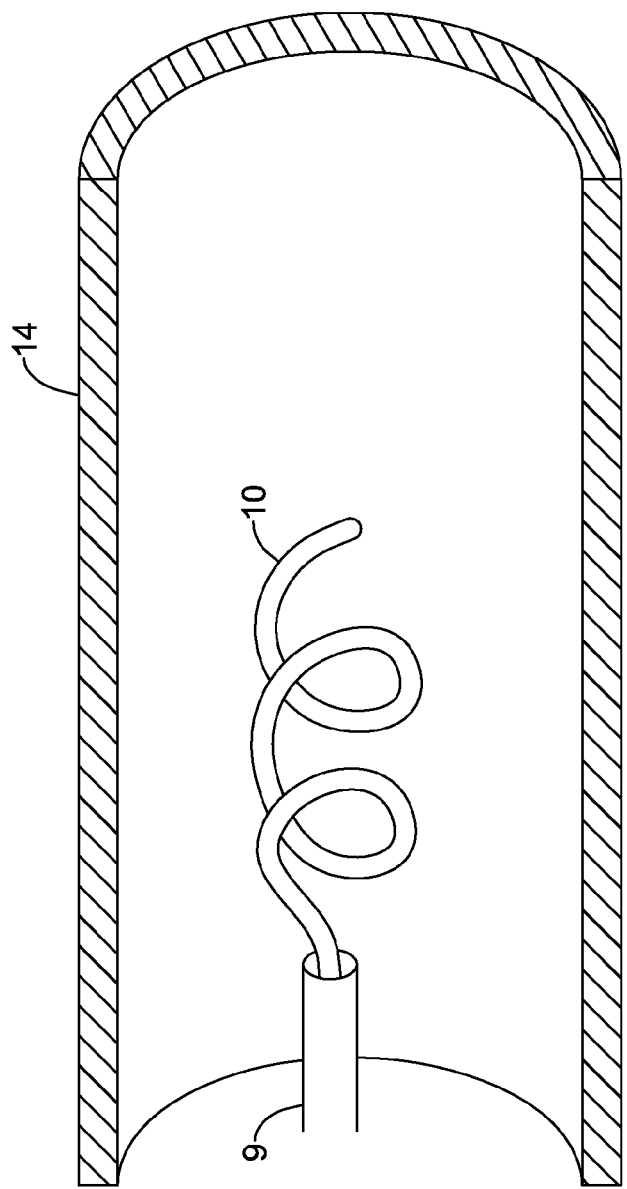
FIG. 8 shows a non-linear electrode.

In the embodiments described thus far, the electrode 10 has been a straight length of wire. However, suitable electrodes can assume any number of shapes. For example an electrode 60 might be helical, as shown in FIG. 8. Such an electrode provides greater surface area for electrical contact, while remaining compact enough to be readily maneuvered.

Electrodes that have a non-linear shape, such as that shown in FIG. 8, can be configured to retract into a sheath. Such retraction enables a surgeon to more easily maneuver the distal tip of the catheter to its destination. In such cases, there exists a mechanism to cause the electrode 10 to assume its desired shape when extended outside of the sheath.

One such mechanism includes an electrode guide-wire made of a shape-memory alloy to which the electrode 10 is mechanically coupled. In such a case, the shape-memory alloy is configured to have, as its remembered shape, the desired shape of the electrode 10. When the electrode guide-wire and the electrode 10 are retracted into the sheath, both are fully extended. When the electrode guide-wire, is extended out of the sheath, it assumes its remembered shape, thereby causing the electrode, to which it is mechanically coupled, to likewise assume that shape. Alternatively, the electrode 10 can itself be made of a shape-memory alloy, in which case no electrode guide-wire is necessary.

Figure 9:
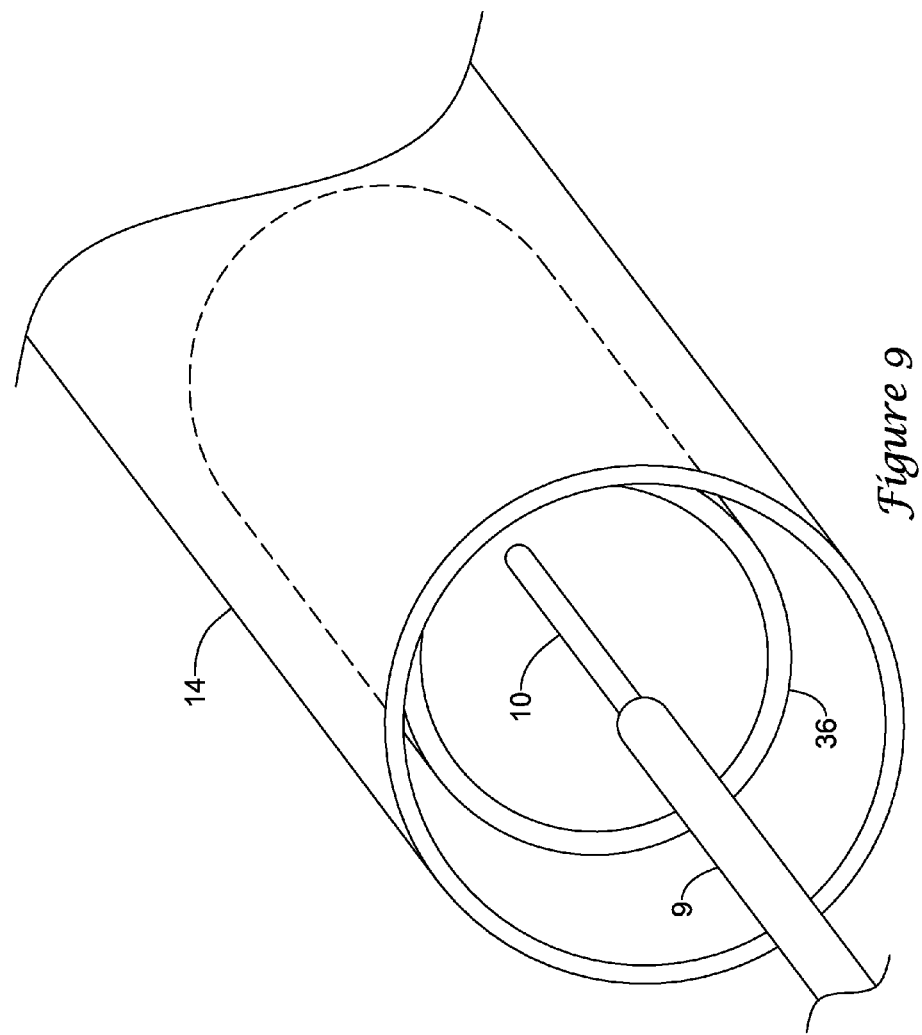
FIG. 9 shows an electrode placed within a lumen defined by a stent.

The first electrode 10 can also be prevented from touching the arterial wall by first implanting an insulated stent 36 in the region in which electrical activation is planned, as shown in FIG. 9. Then, the first electrode 10 is inserted through the artery 14 until it reaches the stent 36. Since the stent 36 is made of an insulating material, it functions as a barrier to current.

Figure 10:
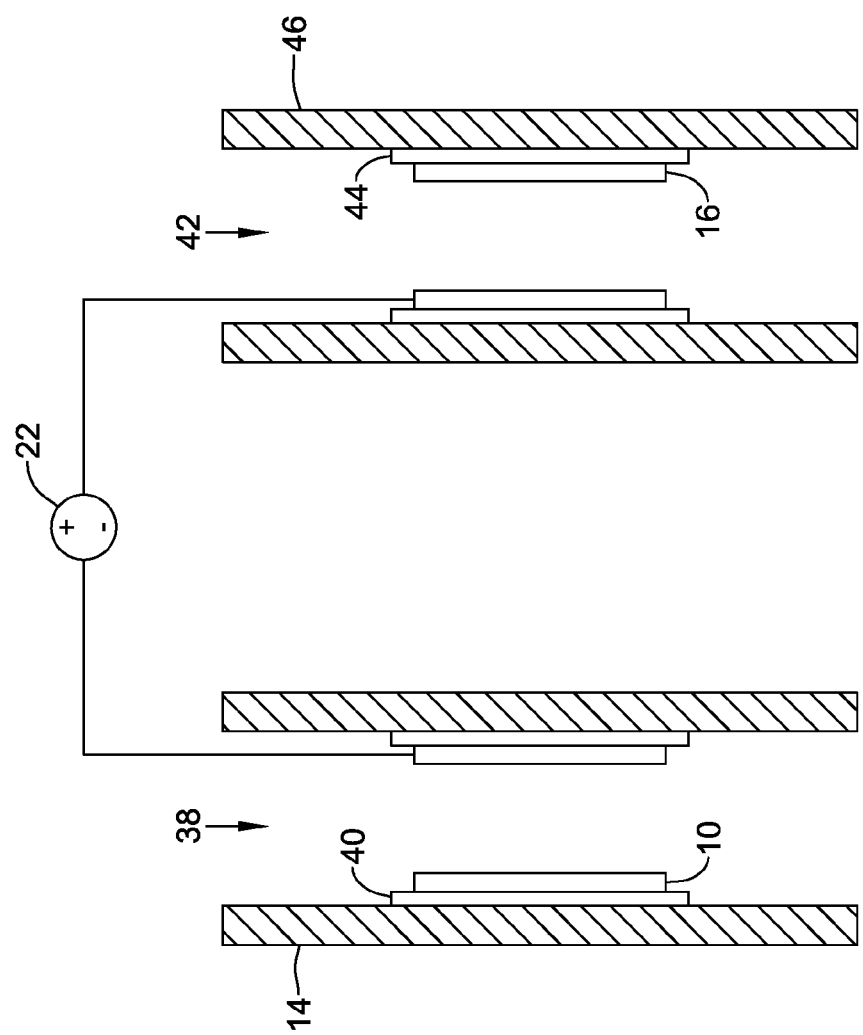
FIG. 10 shows a stimulation system that uses a pair of stents as electrodes.

FIG. 10 shows a longitudinal cross-section of another embodiment in which a stent 38 includes an insulating layer 40 on which is placed a cylindrical first electrode 10. A cylindrical second electrode 16 can be placed on an additional stent 42 having a similar insulation layer and placed in another blood vessel 46 elsewhere in the vascular system. An implanted power supply 22 provides a voltage difference between the two electrodes 10, 16. Stent-mounted electrodes of this type are disclosed in copending U.S. application Ser. No. 10/951,213 filed on Sep. 27, 2004, the contents of which are herein incorporated by reference.

FIG. 9 is representative of a more general configuration in which a first electrode 10 is implanted in an artery feeding a targeted arterial bed, and a second electrode 16 is implanted in a vein draining the targeted arterial bed. The power supply 22, which is typically an energy storage element or battery, together with any control electronics, is mounted near either one of the implanted electrodes 10, 16 and connected to the other implanted electrode 16, 10 with a conductive, insulated wire. Alternatively, the power supply 22 and any control electronics are implanted in a third location and connected to the implanted electrodes 10, 16 by conductive, insulated wires. The power supply 22 can be recharged by an external source of energy, such as an RF transmitter. Alternatively, the power supply 22 can be recharged by an implanted bioelectric generator that transforms body motion or body heat into electrical energy. In some cases, the implanted electrodes 10, 16 are powered entirely from an external power supply 22 such as an RF transmitter. The implanted control electronics may be programmed from outside the body.

As shown in FIG. 1, the second electrode 16 can be a surface electrode, such as a conductive pad placed on the skin. A second electrode 16 placed on the skin is particularly useful for treatment of acute episodes of unwanted vasoconstriction. For treatment of chronic vasoconstriction, the second electrode 16 can be placed in a convenient vein, as suggested by FIG. 10, or in tissue. The relative placement of the first and second electrodes 10, 16 is selected such that the path of least electrical resistance between the two electrodes 10, 16 includes the arterial blood vessels that are to be dilated.

Once the power supply 22 is turned on, a controller 48, shown in FIG. 1, modulates the flow of electric current from the first electrode 10 to the second electrode 16. On its way, the electric current passes through the renal artery 14, and through the remainder of the arterial blood vessels serving the renal system. This electric current flows past smooth muscle cells lining the renal artery 14 and arterioles. The presence of positive charge is believed to hyperpolarize these smooth muscle cells, thereby causing them to relax. This, in turn, would be expected to dilate the arterial blood vessels serving the renal system. As a result, the kidneys 20 would be able to remove excess fluid from the blood even as the remainder of the vascular system remains vasoconstricted.

In the configuration shown in FIG. 1, the polarity of the electric field is such as to hyperpolarize the endothelial cells. Since a change in the membrane potential of the endothelial cells is transmitted across gap junctions to the underlying smooth muscle cells, it is possible to inhibit contraction of the smooth muscle by hyperpolarizing the endothelium alone.

Figure 11:
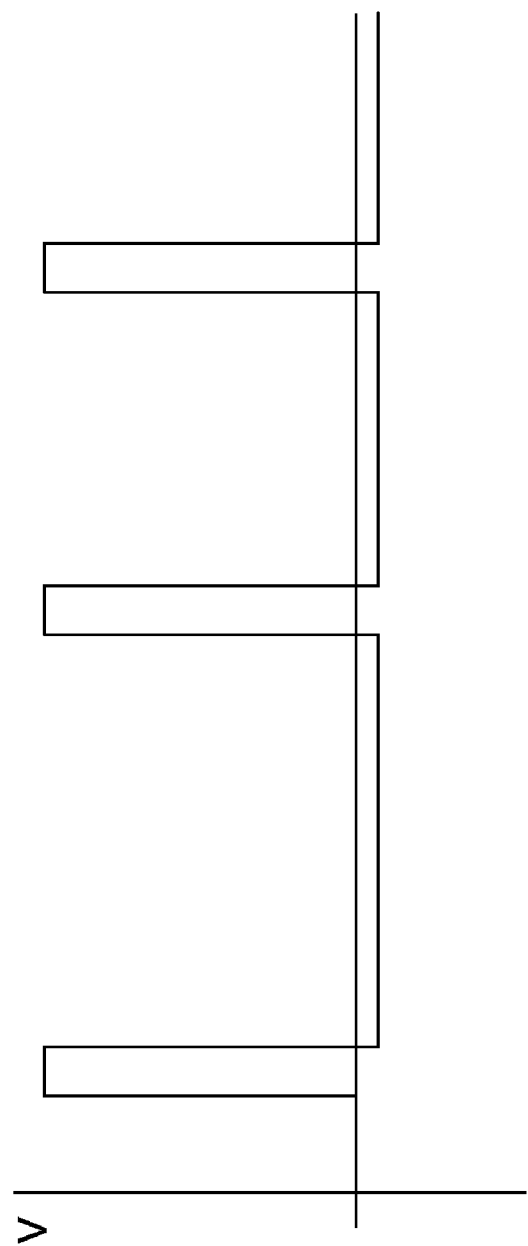
FIG. 11 shows an excitation waveform for use in the stimulation systems of FIGS. 1, 12 and 13.

FIG. 11 shows a typical voltage waveform provided to the first electrode 10. The controller 48 causes the power supply 22 to maintain a large positive voltage during diastole and a small negative voltage at all other times. The optional negative voltage is particularly useful to reduce fouling of the electrode 10. In some practices, the duration of the negative voltage is chosen so that the charge delivered during the negative portion of the waveform balances the charge delivered during the positive portion of the waveform. Suitable voltages are those that cause an electric field of 50 to 2000 volts/meter. Given the conductivity of blood, this translates to current densities of on the order of 25-1000 amperes/meter$^2$. However, some embodiments maintain voltages of 100 to 1000 volts/meter, which translates into current densities of 50-500 amperes/meter$^2$.

In some practices, at least one property of the voltage waveform is synchronized with heart rate. Synchronization can be achieved using locally measured blood flow, blood pressure, or an ECG (electrocardiogram) signal.

The positive voltage is typically applied during a period of low blood flow, which in peripheral arteries occurs primarily during diastole. The application of a positive voltage during diastole is believed to be helpful because the higher fluid velocity associated with systole tends to sweep the larger particles in the blood into the center of the artery. Since most of these particles are negatively charged, the higher fluid velocity already leaves the arterial wall naturally hyperpolarized during systole. In contrast, during diastole, with its slower fluid flow velocity, the negatively charged particles tend to congregate on the wall, thereby tending to neutralize the positive charge on the wall. Thus, it is during diastole that inducing positive charges is most helpful for maintaining hyperpolarization.

The waveform of FIG. 11 can be varied. For example, in some implementations, there is no negative voltage. Instead, the electrode 10 is made neutral. In other implementations, the positive pulse is reduced in amplitude and/or extended in duration. In other implementations, the pulses and the cardiac cycle are asynchronous.

In some applications, the polarity of the electrodes is reversed. In such cases, the stimulation is like that shown in FIG. 11, but with polarities reversed. When polarity is reversed, stimulation is typically performed during systole instead of diastole.

The electrical stimulation can also be delivered in a waveform that may contain shaped features and/or pulses having both positive and negative polarity components at one or more frequencies. The electrical stimulation need not be constant. There may be time intervals during which the stimulation is turned off.

Figure 12:
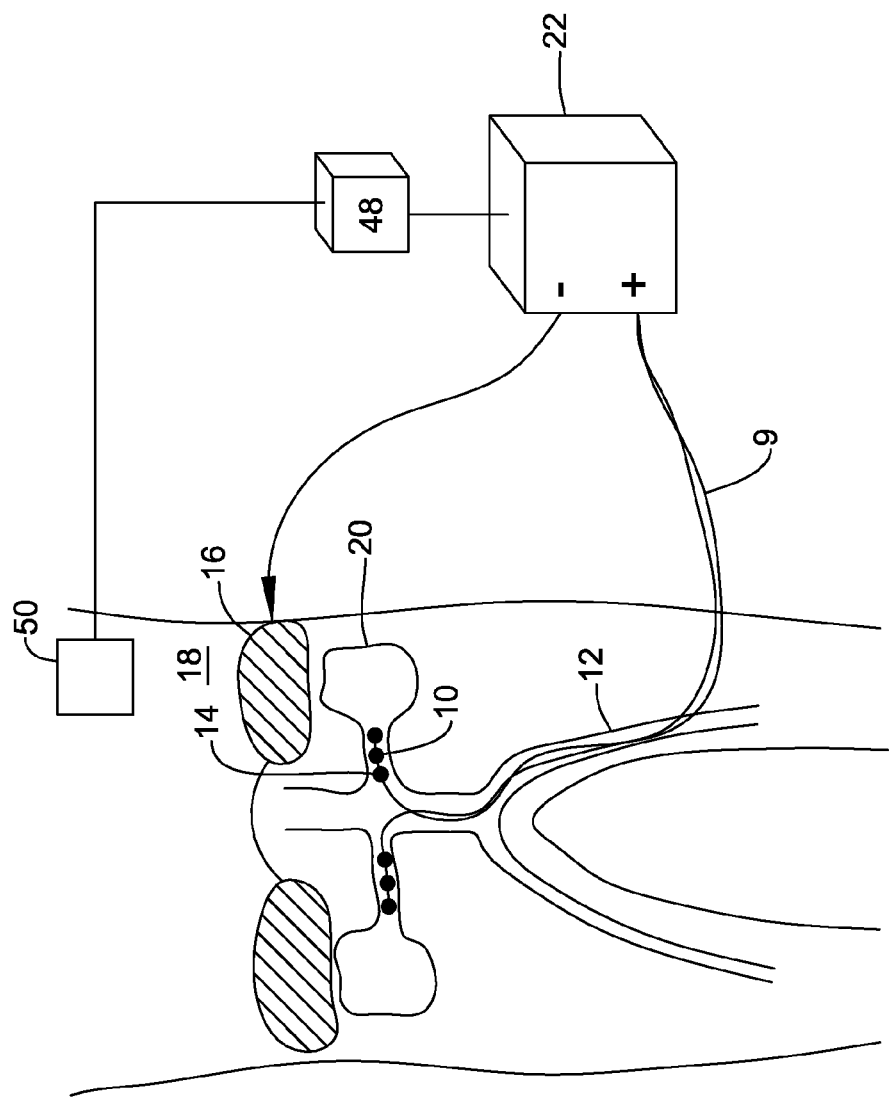

In an alternative embodiment, shown in FIG. 12, the controller 26 is a feedback controller coupled to a sensor 50. The sensor 24 is configured to detect an indicator of the cardiac cycle and to provide cardiac cycle data to the controller 48. Suitable indicators of cardiac cycle include heart beat, blood pressure, flow velocity, or any physical quantity from which the current state of the cardiac cycle can be derived. The controller 48 uses this cardiac cycle data to adaptively vary the interval between the positive pulses shown in FIG. 10. Typical pulse widths range between half the cardiac cycle and 40 milliseconds.

Figure 13:
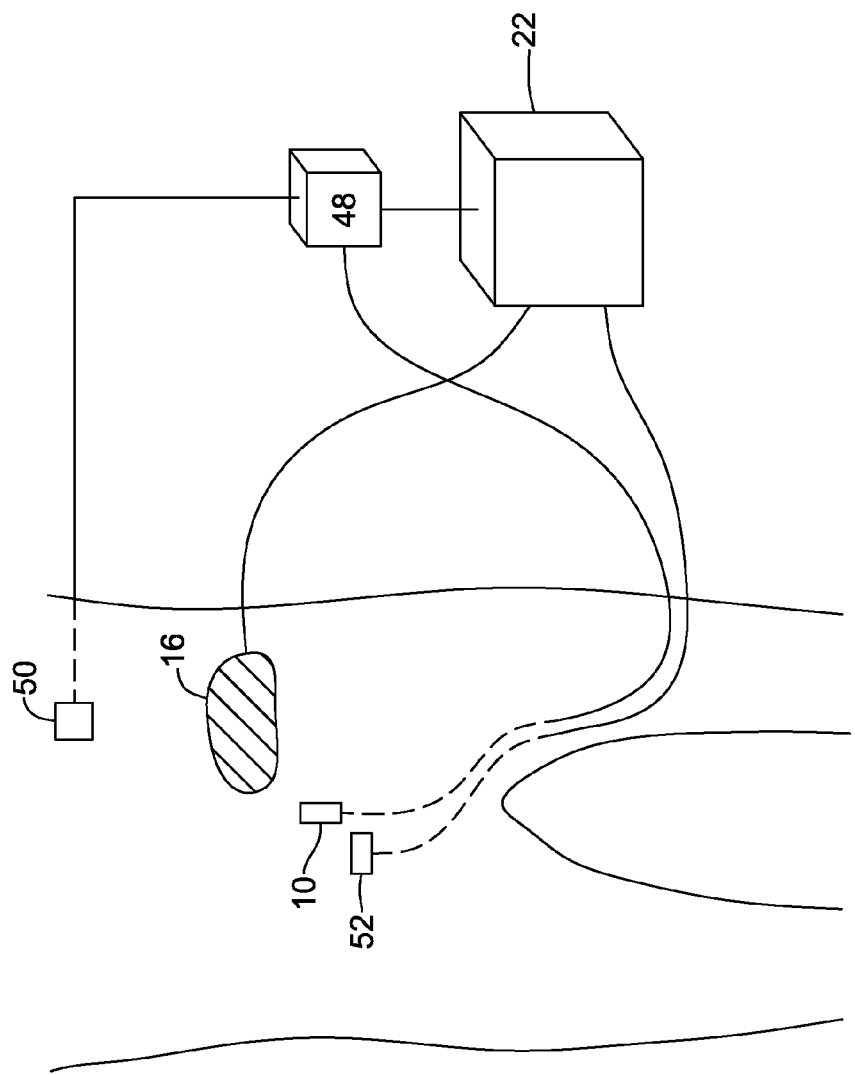

In another embodiment, shown in FIG. 13, the controller 48 receives feedback from a local sensor 52 that measures a property at the target site itself. For example, current flowing in the vicinity of the electrode 10 may have a tendency to heat the surrounding blood. To avoid excessive heating, the local sensor 52 can be a temperature sensor mounted at the distal tip of the catheter. The temperature sensor provides a temperature signal to the controller 48. In response to the temperature signal, the controller 48 regulates the voltage waveform so as to avoid excessive local heating.

Other local characteristics can also be measured by the local sensor 52. For example, the local sensor 52 can be a pressure sensor that provides a pressure signal on the basis of which the controller 48 determines whether a desired local blood pressure has been achieved.

Figure 14:
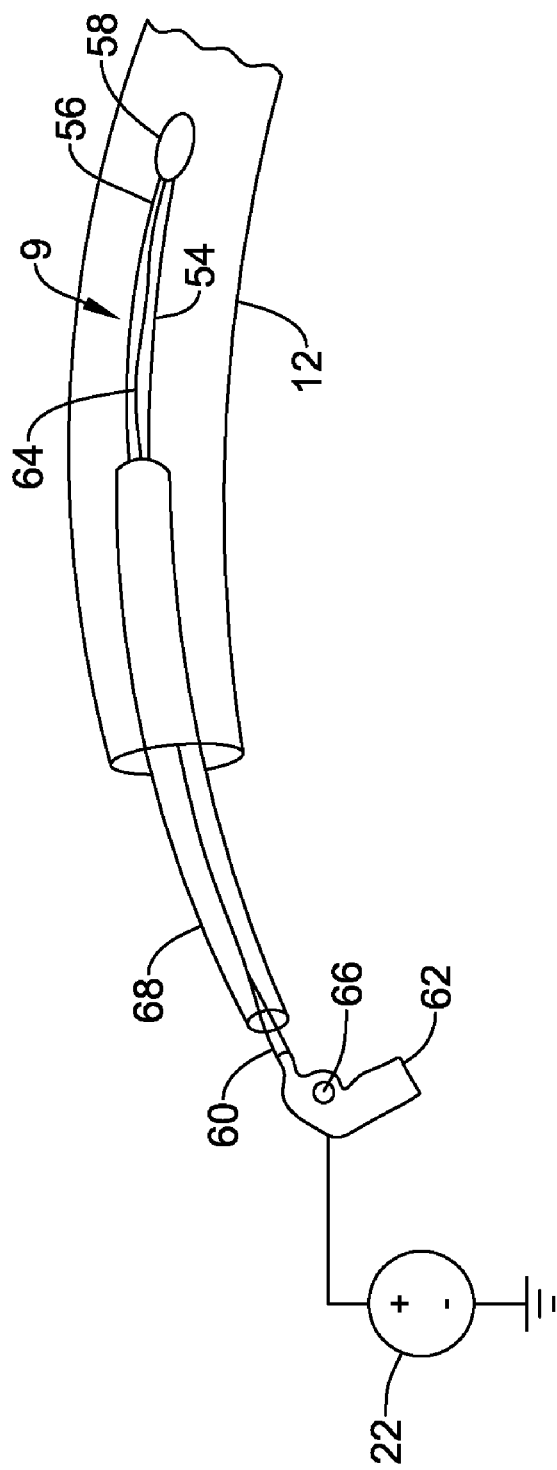
FIG. 14 shows a catheter inserted into a blood vessel.

A typical catheter 9 shown in FIG. 14, features a flexible tube 54 having a distal end 56 connected to a distal tip assembly 58 and a proximal end 60 coupled to a handle 62. Within the distal tip assembly 58 are the first electrode 10 and any of the ancillary structures described above. Extending through the tube 54 is a guide-wire 64, a distal end of which, in some embodiments, also functions as the first electrode 10. A proximal end of the guide-wire 64 is coupled to the handle 62. A trigger 66 mounted on the handle 62 enables a surgeon to selectively connect the power supply 22 to the first and second electrodes 10, 16. Both the catheter 9 and its distal tip assembly 58 are sized and shaped to pass through a cannula 68 inserted into a blood vessel, which in FIG. 14 is the femoral artery 12.

Additional applications of the foregoing configurations include dilating a coronary artery bed distal to an occlusion in patients suffering from acute myocardial infarction. Such dilation may hasten re-perfusion and prevent micro-embolic occlusion of arterioles distal to the occlusion, thereby minimizing loss of myocardium. Dilation of the arterial bed distal to an ischemic stroke may offer the same benefits to affected brain parenchyma. Dilation of vascular beds supplying the lung, for example by an electrode implanted into the pulmonary artery, is useful for treatment of primary pulmonary hypertension. On-demand dilation of penile arteries using a remote-controlled implanted stimulator may help resolve male sexual dysfunction. Systemic hypertension may be controlled by dilation of selected peripheral arterial beds. In this application, implanted electrodes may stimulate dilation in response to an implanted blood pressure sensor, or via remote programming of implanted control circuitry.

In other applications, electrical stimulation can be applied to autonomic nerves to treat a variety of disorders. In such applications, the first and second electrodes 10, 16 are placed near damaged tissue enervated by autonomic nerves. The electrodes 10, 16 are brought near the region either by passing them through a blood vessel that serves that damaged tissue, or by direct insertion into the damaged tissue. Electrical stimulation can be applied to sympathetic or parasympathetic efferent nerves to stimulate or relax tissues respectively, or to afferent nerves to demand attention from the brain or to block signals such as pain from reaching the brain.

For example the apparatus of the present invention can be used to block pain signals originating in nociceptive nerves. When connected to the terminals of the power supply 22, the electrodes 10, 16 cause current to flow into the tissue. This current hyperpolarizes the nociceptive nerves, thereby preventing them from depolarizing. Since the nociceptive nerves provide the sensation of pain to the brain, this hyperpolarization brings about a cessation, or significant diminution, of pain. In addition, current delivered through arterial blood vessels feeding the injured tissue dilates those blood vessels. As a result, more blood is available to nourish the injured tissue, thereby promoting its healing.

The foregoing method of increasing blood supply to nourish selected tissue can be reversed in cases in which one wishes to retard blood flow to, or growth of selected tissue. Reversal of polarity negatively charges the blood vessel wall, thereby reducing the magnitude of the membrane potential, and potentially causing vasoconstriction. It is additionally possible to induce local constriction at the site of the stimulating electrode by stimulating the sympathetic nerve that constricts the smooth muscle. By selectively constricting arteries, one can reduce flow of arterial blood to selected tissues, thereby inhibiting growth of, and perhaps causing ischemic death of those tissues. This is particularly useful when the selected tissue is, for example, a cancerous tumor, particularly, one that has yet to metastasize. Yet another application of selective vasoconstriction is that of inducing vasoconstriction to reduce blood flow to one or more arteries feeding the site of hemorrhage. This is particularly useful for treating a hemorrhagic stroke.

An apparatus as described herein can be used to deliver a variety of therapies in the acute hospitalization setting. Such therapies include, but are not limited to: selective dilation of one or both renal arterial beds to increase urine output and reduce blood volume; dilation of an arterial bed distal to a blockage in a coronary, cerebral or other artery to provide increased blood flow to ischemic tissue following removal of the offending stenosis, and to allow flushing and passage of micro-emboli through small blood vessels distal to the blockage; and vasoconstriction of arteries feeding the site of a hemorrhagic stroke.

Implanted electrodes as described herein can also be used to deliver therapy chronically or periodically. Such therapies include, but are not limited to: vasodilation of selected peripheral arterial beds to treat systemic hypertension; vasodilation of selected arterial beds to treat local hypertension, for example primary pulmonary hypertension; vasodilation of the penile arteries to treat male sexual dysfunction; and vasoconstriction of an arterial bed feeding a tumor to treat cancer.

Having described the invention, and a preferred embodiment thereof, what we claim as new, and secured by Letters Patent is:

1. An apparatus for locally controlling smooth muscle tone for a plurality of arterioles within an arterial bed, the apparatus comprising:

a first electrode for insertion into an artery;

a barrier for preventing the first electrode from contacting an arterial wall;

a second electrode configured to be positioned to use blood vessels as communication channels to cause current flowing through conductive blood between the first and second electrodes to traverse the plurality of arterioles in the arterial bed and control smooth muscle tone for the plurality of arterioles;

a power supply;

an electronic controller for coupling the power supply to the electrodes, the controller being configured to use the electrodes to maintain a waveform for controlling polarization of smooth muscle tone for the plurality of arterioles in the arterial bed; and a sensor coupled to the controller, wherein the sensor is configured to provide data indicative of the cardiac cycle to the controller;

wherein the controller is configured to generate the waveform and to synchronize the waveform with the cardiac cycle in response to the data such that a positive voltage is applied during ventricular diastole.

2. The apparatus of claim 1, wherein the first electrode comprises a stent.

3. The apparatus of claim 1, wherein the first electrode comprises a distal tip of a catheter.

4. The apparatus of claim 1, wherein the second electrode comprises conducting pads for placement on the skin of a patient.

5. The apparatus of claim 1, wherein the second electrode comprises a distal tip of a catheter.

6. The apparatus of claim 1, wherein the barrier comprises a stent defining a lumen for receiving the first electrode.

7. The apparatus of claim 1, wherein the barrier comprises a housing surrounding the first electrode.

8. The apparatus of claim 1, wherein the barrier comprises a cage surrounding the first electrode.

9. The apparatus of claim 1, wherein the controller is configured to generate a waveform having pulses of alternating polarity.

10. The apparatus of claim 1, wherein the controller is configured to generate a waveform having pulses of a single polarity.

11. The apparatus of claim 1, wherein the sensor is a local sensor configured to provide data indicative of blood pressure local to the first electrode.

12. An apparatus for locally controlling smooth muscle tone for a plurality of arterioles within an arterial bed, the apparatus comprising:

a first electrode for insertion into an artery;

a barrier for preventing the first electrode from contacting an arterial wall;

a second electrode configured to be positioned to use blood vessels as communication channels to cause current flowing through conductive blood between the first and second electrodes to traverse the plurality of arterioles in the arterial bed and control smooth muscle tone for the plurality of arterioles;

a power supply; and an electronic controller for coupling the power supply to the electrodes, the controller being configured to use the electrodes to maintain a waveform for controlling polarization of smooth muscle tone for the plurality of arterioles in the arterial bed;

wherein the first electrode comprises a distal tip of a catheter;

wherein the barrier comprises a housing surrounding the first electrode; and a local sensor for providing data indicative of blood pressure local to the first electrode, wherein the controller is configured to manipulate the waveform in response to the data provided by the local sensor.

13. The apparatus of claim 12, wherein the controller is configured to generate a waveform that is synchronized with the cardiac cycle.

14. The apparatus of claim 13, wherein the waveform has pulses of alternating polarity.

15. The apparatus of claim 13, wherein the waveform has pulses of a single polarity.

16. The apparatus of claim 13, wherein the waveform has an excitation cycle that overlaps the diastole portion of the cardiac cycle.

17. The apparatus of claim 16, wherein the waveform has a positive voltage during the excitation cycle.

* * * * *